United States Patent
Zhao et al.

(10) Patent No.: US 10,577,463 B2
(45) Date of Patent: Mar. 3, 2020

(54) NCO-FREE COMPOUNDS AND USAGE THEREOF IN A CURABLE COMPOSITION

(71) Applicants: Henkel AG & Co. KGaA, Duesseldorf (DE); Henkel IP & Holding GmbH, Duesseldorf (DE)

(72) Inventors: Ligang Zhao, Duesseldorf (DE); Roberto Pela, Duesseldorf (DE); Weifeng Dai, Tarragona (ES); Ciaran Mcardle, Dublin (IE); Eva Maria Alcazar, Tarragona (ES); Maria Merce Bertomeu, Tarragona (ES); Nils Bongartz, Haan (DE); Jun Liu, Tarragona (ES)

(73) Assignees: Henkel AG & CO. KGaA, Duesseldorf (DE); Henkel IP & Holding GmbH, Duesseldorf (DE)

( * ) Notice: Subject to any disclaimer, the term of this patent is extended or adjusted under 35 U.S.C. 154(b) by 255 days.

(21) Appl. No.: 15/472,523

(22) Filed: Mar. 29, 2017

(65) Prior Publication Data
US 2017/0198095 A1    Jul. 13, 2017

Related U.S. Application Data

(63) Continuation of application No. PCT/EP2015/072622, filed on Sep. 30, 2015.

(30) Foreign Application Priority Data

Sep. 30, 2014 (EP) ..................... 14187164

(51) Int. Cl.
| | | |
|---|---|---|
| *C08G 71/04* | (2006.01) | |
| *C08G 18/83* | (2006.01) | |
| *C08L 75/04* | (2006.01) | |
| *C08G 18/73* | (2006.01) | |
| *C08G 18/48* | (2006.01) | |
| *C08G 18/10* | (2006.01) | |
| *C08G 18/75* | (2006.01) | |
| *C07C 271/06* | (2006.01) | |
| *C07C 275/26* | (2006.01) | |
| *C08G 71/02* | (2006.01) | |
| *C09D 175/02* | (2006.01) | |
| *C09D 175/12* | (2006.01) | |
| *C09J 175/02* | (2006.01) | |
| *C09J 175/12* | (2006.01) | |

(52) U.S. Cl.
CPC ............ *C08G 71/04* (2013.01); *C07C 271/06* (2013.01); *C07C 275/26* (2013.01); *C08G 18/10* (2013.01); *C08G 18/4854* (2013.01); *C08G 18/73* (2013.01); *C08G 18/755* (2013.01); *C08G 18/83* (2013.01); *C08G 71/02* (2013.01); *C08L 75/04* (2013.01); *C09D 175/02* (2013.01); *C09D 175/12* (2013.01); *C09J 175/02* (2013.01); *C09J 175/12* (2013.01)

(58) Field of Classification Search
CPC .. C08G 18/4854; C08G 18/73; C08G 18/755; C08G 18/83; C08G 18/10; C08L 75/04; C09J 175/12; C09J 175/02
USPC ........................................................ 524/592
See application file for complete search history.

(56) References Cited

U.S. PATENT DOCUMENTS

| | | |
|---|---|---|
| 3,383,403 A | 5/1968 | Pollart |
| 3,872,152 A | 3/1975 | Kehr et al. |
| 4,312,798 A | 1/1982 | Kovacs |
| 5,591,890 A | 1/1997 | Jacobson |
| 6,809,160 B2 | 10/2004 | Tsuboniwa et al. |
| 8,426,357 B2 | 4/2013 | Kraehmer et al. |
| 9,260,467 B2 | 2/2016 | Brossmer et al. |
| 2003/0225239 A1 | 12/2003 | Nakamura et al. |
| 2013/0115405 A1 | 5/2013 | Kinzelmann et al. |

FOREIGN PATENT DOCUMENTS

| | | |
|---|---|---|
| GB | 1366723 A | 9/1974 |
| JP | 2002161126 A | 6/2002 |
| JP | 2005097607 A | 4/2005 |
| JP | 2010519182 A | 6/2010 |
| WO | 2011160912 A1 | 12/2011 |
| WO | 2013065009 A1 | 5/2013 |
| WO | 2013097942 A1 | 7/2013 |

OTHER PUBLICATIONS

Babajide O. Okandeji et al: "Bronsted Acidity of Substrates Influences the Outcome of Passerini Three-Component Reactions", the Journal of Organic Chemistry, vol. 74, No. 14, Jul. 17, 2009, pp. 5067-5070.

Macromolecules 1995, 28, 6020-6025, polyaddition of bifunctional acetylene containing electron withdrawing groups.

International Search Report for International PCT Patent Application No. PCT/EP2015/072622 dated Dec. 14, 2015.

(Continued)

*Primary Examiner* — Doris L Lee
(74) *Attorney, Agent, or Firm* — James E. Piotrowski

(57) ABSTRACT

The invention relates to a compound comprising at least two —(NH—C=O)— groups and at least two —(C=O)—C≡C—R$^1$ groups, wherein R$^1$ represents hydrogen or a group having from 1 to 12 carbon atoms; a curable composition comprising a first unit comprising at least two —(NH—C=O)— groups, a second unit comprising at least two —(C=O)—C≡C—R$^1$ groups, and a catalyst; and the use of the composition as an adhesive, coating, casting composition or as sealant.

19 Claims, No Drawings

(56) References Cited

OTHER PUBLICATIONS

Gupta et al., "A Bioorthogonal Chemoenzymatic Strategy for Defined Protein Dendrimer Assembly," ChemBiochem Communications, 2012, 13, pp. 2489-2494.
Chen et al., "Facile Synthesis of Cyclopeptide-Centered Multivalent Glycoclusters with 'Click Chemistry' and Molecular Recognition Study by Surface Plasmon Resonance," Bioorganic & Medicinal Chemistry Letters, 2009, 19, pp. 3775-3778.
Baklouti et al., "Synthesis of Ethynyl-Substituted Benzoyl Chlorides and of Related a,w-Ethynyl Oligomers," Tetrahedron Letters, 1992, vol. 33, No. 11, pp. 1451-1454.

NCO-FREE COMPOUNDS AND USAGE THEREOF IN A CURABLE COMPOSITION

The present invention relates to essentially NCO-free compounds preferably with urea and/or urethane groups, a curable composition comprising these compounds and the use of the composition.

Commonly, polyurethane prepolymers as used for moisture curable compositions are prepared by reacting a polyisocyanate with a polyol or a mixture of polyols. In this reaction, the NCO:OH ratio of the polyisocyanate and the polyol is larger than 1 and the resulting urethane prepolymers are NCO-terminated and are very moisture sensitive. A further disadvantage of such prepolymers is that they comprise unreacted monomeric polyisocyanates. These monomers are contained in small quantities only, but are still physiologically objectionable because through the reaction with moisture, primary amines are yielded, in particular primary aromatic amines.

From the state of the art, several methods for preparing NCO-free polyurethane prepolymers are known. However, the resulting polymers often lack the properties of the "normal" polyurethanes. In particular, the thermal stability is lower than desired.

For example, WO 2011/160912 A1 discloses a hot melt adhesive containing thermoplastic polyurethanes. These polyurethanes are made up from polyols and isocyanates, wherein for the synthesis of the thermoplastic polyurethanes a NCO:OH ratio below 1 is implemented, resulting in a polymer which is not NCO-terminated and does not contain any unreacted monomeric isocyanates.

However, due to the lack of the NCO-groups which are responsible for the curing reaction, thermoplastic urethanes are not reactive/not curable under common conditions.

It is therefore an object of the present invention to provide curable essentially NCO-free compounds usable to prepare curable NCO-free compositions preferably based on polyurethanes.

This object is, inter alia, solved by a compound comprising at least two —(NH—C=O)— groups and at least two —(C=O)—C≡C—$R^1$ groups, wherein $R^1$ represents hydrogen or a group having from 1 to 12 carbon atoms, preferably hydrogen or $CH_3$, and most preferred hydrogen.

$R^1$ can be the same or different for the different —(C=O)—C≡C—$R^1$ groups. Preferably $R^1$ is the same for all —(C=O)—C≡C—$R^1$ groups.

In a preferred embodiment, this compound is obtainable by a) reacting a polyisocyanate with at least two isocyanate groups with a polyol or a polyamine or a mixture thereof to form an intermediate, wherein the molar ratio of the NCO groups of the polyisocyanate to the sum of hydroxyl groups, primary amino groups and secondary amino groups of the polyol and polyamine is less than 1, for example from 0.2:1 to 0.99:1, in particular from 0.25:1 to 0.75:1, more preferably from 0.4:1 to 0.6:1 and most preferably 1:2, b) reacting a compound of the formula $R^2O$—(C=O)—C≡C—$R^1$ with the intermediate of step a) in molar excess to the sum of hydroxyl groups, primary amino groups and secondary amino groups of the intermediate, wherein $R^1$ represents hydrogen or a group having from 1 to 12 carbon atoms, preferably hydrogen or $CH_3$, and most preferred hydrogen, and wherein $R^2$ represents hydrogen or a group having from 1 to 4 carbon atoms, preferably hydrogen or $CH_3$, and most preferred hydrogen, and mixtures thereof.

With regard to the compound of the formula $R^2O$—(C=O)—C≡C—$R^1$ it is noted that it is also possible to use mixtures of different compounds with different residues $R^1$ and/or $R^2$.

It is essential that the molar ratio of the polyisocyanate to the sum of hydroxyl groups, primary amino groups and secondary amino groups of the polyol and polyamine is less than 1 to ensure that the compound is essentially not NCO-terminated and that the compound, after reaction is complete, does essentially not contain any unreacted isocyanate monomers. In other words, the free NCO groups of the isocyanates are essentially completely reacted with, for example, the polyol; in this case the compound is essentially fully OH-terminated.

Assuming that a diisocyanate and a diol are used as starting materials, a compound with two terminal OH groups can, theoretically, be formed as an intermediate. In case a polyisocyanate with three NCO groups and a diol are used as starting materials, a compound with three terminal OH groups can, theoretically, be formed as an intermediate.

In step b), the terminal OH groups (in case polyol and no polyamine is used as starting material) of the polyol chains of the intermediate from step a) are reacted with a compound (or a mixture of compounds) of the formula $R^2O$—(C=O)—C≡C—$R^1$. In case the intermediate comprises two terminal OH groups, both of them are reacted with $R^2O$—(C=O)—C≡C—$R^1$, in case a polyisocyanate with three NCO groups was used as starting material for the intermediate, it is sufficient that two of the three OH groups are reacted with $R^2O$—(C=O)—C≡C—$R^1$. It is however preferred that all of the terminal groups of the intermediate (—OH and/or —NH groups) are reacted with $R^2O$—(C=O)—C≡C—$R^1$.

With regard to $R^1$ representing a group having from 1 to 12 carbon atoms, $R^1$ can be a linear or branched, saturated, unsaturated or aromatic hydrocarbon group. $R^2$ representing a group having from 1 to 4 carbon atoms can also be linear, branched, saturated or unsaturated.

As mentioned above, the structure of the inventive compound depends on the structure of the starting materials (branched, linear) and the number of functional groups of the separate starting materials, wherein it is preferred that the inventive compound is linear, i.e. it is preferred to use starting materials which result in a linear compound.

Furthermore, the structure of the inventive compound depends on the molar ratio of the NCO groups of the polyisocyanate to the sum of hydroxyl groups, primary amino groups and secondary amino groups of the polyol and polyamine. In case a 1:2 ratio is used, the inventive compound might be based on one central polyisocyanate, each former NCO group being coupled to one polyol/polyamine. In case the ratio is between 1:2 and 1, the compound may comprise, for example, two polyisocyanate and three polyol moieties, wherein the number of —(NH—C=O)— groups of course depends on the exact structure of the inventive compound.

Surprisingly, it was discovered that a composition, comprising the inventive compound and at least a catalyst, cures very quickly, even at room temperature. Furthermore, it was found that the resulting cured composition has a very high thermal stability (in most instances the thermal decomposition temperature is higher than 300° C.)

A further advantage of the inventive compounds/compositions is that the properties of the cured compositions, like elongation at break and tensile strength, can be adjusted to cover a very broad range by simply adapting the polyols/polyamines and/or the isocyanate.

The —(NH—C=O)— groups are preferably provided by the urea group and/or the urethane group (i.e. the —(NH—C=O)— groups are part of/contained in urea and/or urethane groups) depending on the starting materials in step a), wherein it is preferred that the —(NH—C=O)— groups are provided by a urethane group. For example, when using i) a diisocyanate and ii) a polyol as starting materials, the —(NH—C=O)— groups of the intermediate will be provided by urethane groups, wherein the exact number of the urethane groups depend on the reaction conditions (e.g. NCO:OH ratio). In any case the intermediate comprises at least two urethane groups.

In the context of the present invention each urethane with two or more urethane groups is referred to as "polyurethane", i.e. this term refers to a defined polyurethane structure, as is obtained from a targeted one-step or multi-step polyurethane synthesis. The term shall include all variations of this structure, as they result from the statistical nature of the polyaddition process.

In case a 1:1 mixture of a polyol/a polyamine is used, the intermediate can comprise urethane and urea groups, wherein the exact distribution of the urea and urethane groups depends on reaction rates of the polyol/polyamine with the polyisocyanate. In case they differ significantly, it is for example possible that the intermediate comprises different compounds with different distributions of urea and urethane groups. It is also possible to use mixtures of polyols and/or polyamines. In case 100% polyamine is used, the intermediate is a polyurea. For the term "polyurea" the same applies as for the term "polyurethane".

With regard to the polyol, a wide range of polyols can be used, for example, aliphatic polyols, polyester polyols, polyether polyols, polycarbonate polyols, polycaprolactone polyols, polybutadiene polyols, polysulfide polyols and mixtures thereof.

However, it is preferred to use a polyol with terminal OH groups, preferably selected from a group comprising polyether polyols, polyether polyol block-copolymers (e.g. poly(ethylene gycol)-block-poly(propylene glycol)-block-poly(ethylene glycol), poly(propylene glycol)-block-poly(ethylene glycol)-block-poly(propylene glycol)), polyester polyols (aromatic and non-aromatic), polyester polyol block-copolymers (e.g. (polycaprolactone-block-polytetrahydrofurane-block-polycaprolactones)) or mixtures thereof.

The kind of polyol/polyamine and the molecular weight of the polyol/polyamine have a huge impact on the properties of the compound. For example, higher molecular weight polyols (molecular weights from 2,000 to 10,000) are used to make more flexible polyurethanes while lower molecular weight polyols make more rigid products. In connection with the inventive compounds and the inventive composition it is preferred that the number average molar weight ($M_n$) of the polyol is at least 200, preferably from 200 to 20000 and most preferred from 1000-5000 g/mol.

The molecular weights refer to number average molecular weights (Mn), unless otherwise stipulated. All molecular weight data refer to values obtained by gel permeation chromatography (GPC), unless otherwise stipulated, e.g. according to DIN 55672.

Preferred polyols are selected from a group comprising polyethylene glycol (PEG), polypropylene glycol (PPG) and polytetrahydrofuran (pTHF), and mixtures thereof.

With regard to the polyisocyanates, the present invention is not limited to special isocyanates as long as the isocyanate comprises at least two NCO groups (in the context of the present invention, the term polyisocyanate therefore refers to isocyanates with two or more NCO groups). Examples of these compounds with two NCO groups have the general structure O=N=C—Z—C=N=O, wherein Z may be a linear or branched aliphatic, alicyclic, cycloaliphatic or aromatic hydrocarbon group.

Suitable polyisocyanates are aromatic, aliphatic, alicyclic or cycloaliphatic polyisocyanates. These can be selected, for example, from 4,4'-diphenylmethane diisocyanate (MDI), hydrogenated MDI (H12MDI), partly hydrogenated MDI (H6MDI), xylylene diisocyanate (XDI), tetramethylxylylene diisocyanate (TMXDI), 4,4'-diphenyldimethylmethane diisocyanate, dialkylenediphenylmethane diisocyanate, tetraalkylenediphenylmethane diisocyanate, 4,4'-dibenzyl diisocyanate, 1,3-phenylene diisocyanate, 1,4-phenylene diisocyanate, the isomers of toluylene diisocyanate (TDI), 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane (IPDI), tetramethoxybutane-1,4-diisocyanate, naphthalene-1,5-diisocyanate (NDI), butane-1,4-diisocyanate, hexane-1,6-diisocyanate (HDI), dicyclohexylmethane diisocyanate, 2,2,4-trimethylhexane-2,3,3-trimethylhexamethylene diisocyanate, cyclohexane-1,4-diisocyanate, ethylene diisocyanate, methylenetriphenyltriisocyanate (MIT), phthalic acid bisisocyanatoethyl ester, trimethylhexamethylene diisocyanate, 1,4-diisocyantobutane, 1,12-diisocyanatododecane, and dimer fatty acid diisocyanate, lysine ester diisocyanate, 4,4-dicyclohexylmethane diisocyanate, 1,3-cyclohexane or 1,4-cyclohexane diisocyanate, and mixtures thereof.

Suitable trifunctional isocyanates can be obtained by trimerization or oligomerization of diisocyanates, or by reacting diisocyanates with trifunctional hydroxyl-group-containing compounds. Examples thereof are trimerization products of the isocyanates HDI, MDI, or IPDI, or adducts of diisocyanates and low-molecular-weight triols, such as trimethylolpropane or glycerol.

It is preferred that the polyisocyanate is selected from a group comprising 2,4-toluene diisocyanate, 2,6-toluene diisocyanate, 4,4'-diphenylmethane diisocyanate, 2,4'-diphenylmethane diisocyanate, 2,2'-diphenylmethane diisocyanate, isophorone diisocyanate, hexamethylene diisocyanate, 4,4'-methylene dicyclohexyl diisocyanate, 2,4'-methylene dicyclohexyl diisocyanate, 2,2'-methylene dicyclohexyl diisocyanate, and mixtures thereof.

In the scope of the present invention, polyamines are also suitable for manufacturing the inventive compound. Polyethers having terminal amino groups are suitable examples for this.

Suitable polyamines can also be compounds having more than two functional groups, i.e. which have more than two primary and/or secondary amino groups. Examples of these compounds are ethylene diamine, 1,2-propylenediamine, 1,3-propylenediamine, butylenediamines, pentamethylenediamines, hexamethylenediamines (1,6-diaminohexane), alkylhexamethylenediamine such as 2,4-dimethylhexamethylenediamine, alkylenediamines in general having up to about 44 carbon atoms, wherein also cyclic or polycyclic alkylenediamines can be used such as for example those that can be obtained in the known manner from the dimerization products of unsaturated fatty acids. Aromatic diamines, such as for example 1,2-phenylenediamine, 1,3-phenylenediamine or 1,4-phenylenediamine can also be used, but are not preferred. Furthermore, higher amines such as e.g. diethylenetriamine, aminomethyl-1,8-diaminooctane and triethylenetetramine can be used in the scope of the invention.

It is preferred to use a polyamine selected from a group comprising ethylene diamine, 1,2-diaminopropane, 1,4-diaminobutane, 1,3-diaminopentane, 1,6-diaminohexane, 2,5-diamino-2,5-dimethylhexane, 2,2,4- and/or 2,4,4-trimethyl-1,6-diaminohexane, 1,11-diaminoundecane, 1,12-diaminododecane, 1,3- and/or 1,4-cyclohexane diamine, 1-amino-3,3,5-trimethyl-5-aminomethyl-cyclohexane, 2,4' and/or 4,4'-diaminodicyclohexyl methane, 3,3'-dialkyl-4,4'-diamino-dicyclohexyl methanes, polyoxyalkylene polyamines, cycloaliphatic polyamines, polyimines, polyamides, and mixtures thereof.

In connection with the inventive compounds and the inventive composition it is preferred that the number average molar weight ($M_n$) of the polyamine is at least 200, preferred from 200 to 20000 and most preferred from 1000 to 5000 g/mol.

The inventive compounds can be prepared by a method comprising the steps of a) reacting an polyisocyanate with at least two isocyanate groups with a polyol or a polyamine or a mixture thereof to form an intermediate, wherein the molar ratio of the NCO groups of the polyisocyanate to the sum of hydroxyl groups, primary amino groups and secondary amino groups of the polyol and polyamine is less than 1, for example from 0.2:1 to 0.99:1, in particular from 0.25:1 to 0.75:1, more preferably 0.4:1 to 0.6:1 and most preferably 1:2, b) reacting a compound of the formula $R^2O-(C=O)-C\equiv C-R^1$ with the intermediate of step a) in molar excess to the sum of hydroxyl groups, primary amino groups and secondary amino groups of the intermediate, wherein $R^1$ represents hydrogen or a group having from 1 to 12 carbon atoms, preferably hydrogen or $CH_3$, and most preferred hydrogen, and $R^2$ represents hydrogen or a group having from 1 to 4 carbon atoms, preferably hydrogen or $CH_3$, and most preferred hydrogen.

For details with regard to the starting materials and the compound with the formula $R^2O-(C=O)-C\equiv C-R^1$ please see above.

The inventive curable composition comprises a first unit comprising at least two $-(NH-C=O)-$ groups, a second unit comprising at least two $-(C=O)-C\equiv C-R^1$ groups, and a catalyst, wherein $R^1$ represents hydrogen or a group having from 1 to 12 carbon atoms, preferably hydrogen or $CH_3$, and most preferred hydrogen. With regard to $R^1$ representing a group having from 1 to 12 carbon atoms, $R^1$ can be a linear or branched, saturated, unsaturated or aromatic hydrocarbon group. $R^1$ can be the same or different for the different $-(C=O)-C\equiv C-R^1$ groups. Preferably $R^1$ is the same for all $-(C=O)-C\equiv C-R^1$ groups.

In the context of the invention the term "unit" refers to a compound or a part of a compound comprising the unit, i.e. different units can be part of different compounds or the same compound. It is however preferred that the first and the second units are part of different compounds.

Furthermore, it is also possible that the composition comprises a first compound with the first units and a second compound with the second units, wherein the first compound also comprises at least two $-(C=O)-C\equiv C-R^3$ units as the third units, wherein $R^3$ represents hydrogen or a group having from 1 to 12 carbon atoms, preferably hydrogen or $CH_3$, and most preferred hydrogen. With regard to $R^3$ representing a group having from 1 to 12 carbon atoms $R^3$ can be a linear or branched, saturated, unsaturated or aromatic hydrocarbon group and $R^3$ can be the same or different for the different $-(C=O)-C\equiv C-R^3$ groups, preferably $R^3$ is the same for all $-(C=O)-C\equiv C-R^1$ groups. In this case, the composition comprises two compounds with $-(C=O)-C\equiv C-$ units.

It is preferred that the $-(NH-C=O)-$ groups are provided by the urethane and/or the urea group, wherein the precise structure of the first unit comprising the two $-(NH-C=O)-$ groups depends on the starting materials and the reactions rates between the polyisocyanate (or the mixture of different polyisocyanates) and the polyol(s) and/or polyamine(s).

The first and the second units may be part of the same compound, i.e. this compound comprises at least two $-(NH-C=O)-$ groups and at least two $-(C=O)-C\equiv C-R^1$ groups. In this case it is preferred that the compound comprising the first and the second units is a compound as described above. Surprisingly, it was found that a composition comprising the inventive compounds and at least a catalyst cures very quickly, even at room temperature.

Alternatively, the first and the second units are part of different compounds. In this case it is preferred that the first unit is part of/is provided by a thermoplastic polyurethane. As already mentioned above, in this case the compound comprising the first unit may also comprise at least two $-(C=O)-C\equiv C-R^3$ units.

Thermoplastic polyurethanes are very well known to a person skilled in the art and can be formed by reacting polyisocyanates (isocyanates with two or more NCO groups) with polyols, wherein the molar ratio of the isocyanate groups to the OH groups is less than 1. The thermoplastic polyurethane has preferably a number average molecular weight (Mn) from 5,000 to 80,000 g/mol, more preferably from 10,000 to 60,000 g/mol, most preferably from 25,000 to 50,000 g/mol. For example, suitable thermoplastic polyurethane may be prepared with starting materials as described above with regard to the inventive compounds.

Due to this molar excess of the polyol the formed polyurethane essentially does not comprise free NCO groups. Furthermore, the polyurethane does not comprise any free polyisocyanate monomers. Due to the lack of NCO groups, these polyurethanes cannot be cured/cross-linked via these NCO groups; thermoplastic polyurethanes are, compared to the NCO containing polyurethanes, not moisture curing polyurethanes.

The thermoplastic polyurethanes can, however, be cured when the composition comprises the second unit having at least two $-(C=O)-C\equiv C-R^1$ groups.

The exact structure of the compound providing the at least two $-(C=O)-C\equiv C-R^1$ groups is not essential as long as these two groups are present.

It is however preferred that the second unit is provided by a further compound obtainable by reacting a polyether polyol with at least two OH groups with a compound of the formula $R^2O-(C=O)-C\equiv C-R^1$ in a quantity at least equivalent to two OH groups of the polyether polyol, i.e. in a quantity that at least two of the OH groups of the polyether polyol are substituted by $-O-(C=O)-C\equiv C-R^1$, wherein $R^1$ represents hydrogen or a group having 1-12 carbon atoms, preferably hydrogen or $CH_3$, and most preferred hydrogen, and $R^2$ represents hydrogen or a group having 1-4 carbon atoms, preferably hydrogen or $CH_3$, and most preferred hydrogen. With regard to $R^1$ representing a group having 1-12 carbon atoms, $R^1$ can be a linear or branched, saturated, unsaturated or aromatic hydrocarbon group. $R^2$ representing a group having 1-4 carbon atoms can also be linear, branched, saturated or unsaturated.

Depending on the number of $-(NH-C=O)-$ groups of the compound with the first unit, using a polyether polyol with two OH groups/two $-O-(C=O)-C\equiv C-R^1$ groups might lead to a linear polymer, possibly with side chains, when curing the composition (in case the first compound comprises two —(NH—C=O)— groups and no further functional groups useful for a cross-linking).

It is therefore preferred that the second unit is provided by a further compound obtainable by reacting a polyether polyol with at least three OH groups with a compound of the formula $R^2O$—(C=O)—C≡C—$R^1$ in a quantity at least equivalent to three OH groups of the polyether polyol, i.e. in a quantity that three of the OH groups of the polyether polyol are substituted by —O—(C=O)—C≡C—$R^1$, wherein $R^1$ represents hydrogen or a group having 1-12 carbon atoms, preferably hydrogen or $CH_3$, and most preferred hydrogen, and $R^2$ represents hydrogen or a group having 1-4 carbon atoms, preferably hydrogen or $CH_3$, and most preferred hydrogen. With regard to $R^1$ representing a group having 1-12 carbon atoms, $R^1$ can be a linear or branched, saturated, unsaturated or aromatic hydrocarbon group. $R^2$ representing a group having 1-4 carbon atoms can also be linear, branched, saturated or unsaturated.

Using a polyether polyol with at least three OH groups leads to a compound with at least three —O—(C=O)—C≡C—$R^1$ groups. Such a compound can link, for example, three molecules of the compound comprising the first unit —(NH—C—O)— whereby a highly cross-linked structure of the cured composition can be achieved.

With regard to the catalyst it is preferred that the catalyst is a secondary or tertiary amine, preferably the catalyst is selected from a group comprising 1,4-diazabicyclo[2.2.2]octane (DABCO), tetramethylethylenediamine (TMEDA), N,N-diisopropylethylamine (DIPEA), triethanolamine (TEA), tris(2-pyridylmethyl)amine (TPA), tributylamine, 4-dimethylaminophenol (DMAP), N-ethyl-N-methyl propylamine, N-methyl piperidine, N-butyl-4-hydroxy piperidine, 1,8-diazabicyclo[5.4.0]undec-7-ene (DBU), 1,5-diazabicyclo[4.3.0]non-5-ene (DBN), imidazoline, benzimidazole, dimethylamino ethanol (DMAE), pirrole, morpholine, piperidine, piperazine, indole, and mixtures thereof, and most preferred the catalyst is 1,4-diazabicyclo[2.2.2]octane.

The invention also relates to a cured composition obtainable by polymerization of the inventive curable composition and the use of the inventive composition as adhesive, coating, casting composition or as sealant.

EXAMPLES

In some of the following examples, "elongation at break", "tensile strength" and the "decomposition temperature" of cured compositions are indicated.

In the context of the invention, elongation at break refers to the ratio between changed length and initial length after breakage of a tested material (the cured composition). It expresses the capability of a material to resist changes of shape without crack formation. Elongation at break is determined by tensile testing in accordance with EN ISO 527.

Tensile strength refers to the force required to pull a material (the cured composition) to the point where it breaks.

The decomposition temperature (Td) of the cured compositions was measured using thermogravimetric analysis (TGA). At Td a weight loss of 5% is observed. The decomposition temperature was recorded by heating 10° C./min.

Synthesis of the Inventive Compounds

Example 1

Synthesis of isophorone diisocyanate (IPDI) conjugated PTHF diester (hereafter PITHF).

40 g of polytetrahydrofurane (PTHF, Mn=1000 g/mol) was added into a 250 mL 3-neck round-bottom flask and heated at 120° C. under vacuum for 1.5 h. Then, the temperature was cooled down to 90° C. and the reaction mixture was purged with nitrogen (or a comparable inert gas), and 4.45 g of isophorone diisocyanate (IPDI) was added, and the temperature was increased up to 110° C. The reaction mixture was stirred for at least 12 h, until all the NCO groups were consumed, as it was ascertained by titration (the free isocyanate content can, for example, easily be measured by titration of the free isocyanate with an amine and back-titration of the unreacted amine).

42.6 g of the intermediate was added to a round-bottom flask equipped with a Dean-Stark apparatus, together with 0.43 g of p-toluenesulfonic acid (p-TsOH) solved in 100 mL of toluene. The mixture was stirred at 40 to 50° C. until a homogeneous solution was observed, then 5.37 g (4.7 mL) of propiolic acid was added. The final solution was heated up to 140° C. and stirred at this temperature for 48 hours. When the reaction was finished (as detected by $^1$H-NMR) the mixture was cooled down to room temperature, and diluted with another 100 ml of toluene. The organic solution was then washed three times with a solution of sodium bicarbonate in water (2 wt % of bicarbonate in water), until the excess of propiolic acid was neutralized. The organic phase was subsequently treated with brine, dried over magnesium sulfate, filtered and concentrated in vacuum, resulting in the inventive compound.

Example 2

Synthesis of hexamethylene diisocyanate (HDI) conjugated PTHF diester (hereafter PHTHF).

50 g of PTHF (Mn=1000 g/mol) was added into a 250 mL 3-neck round-bottom flask and heated at 120° C. under vacuum for 1.5 h. Then, after the temperature was cooled down to 90° C. and purged with nitrogen, and 4.21 g of hexamethylene diisocyanate (HDI) was added, and the temperature was increased up to 110° C. The reaction mixture was stirred for at least 12 h, until all the NCO groups were consumed, as it was confirmed by titration.

52.47 g of the intermediate was added to a round-bottom flask equipped with a Dean-Stark apparatus, together with 0.52 g of p-toluenesulfonic acid (p-TsOH) solved in 100 mL of toluene. The mixture was stirred at 40 to 50° C. until a homogeneous solution was observed, and then, 6.38 g (5.67 mL) of propiolic acid was added. The final solution was heated up to 140° C. and stirred at this temperature for 48 hours. When the reaction was finished (as detected by $^1$H-NMR) the mixture was cooled down to room temperature, and diluted with another 100 ml of toluene. The organic solution was then washed three times with a solution of sodium bicarbonate in water (2% of bicarbonate in water), until the excess of propiolic acid was neutralized. The organic phase was subsequently treated with brine, dried over magnesium sulfate, filtered and concentrated in vacuum, resulting in the inventive compound. Final yield: 70%.

Inventive Composition/Curing of the Composition

Example 3

Composition with compound from Example 1 (PITHF) and additional compound.

2 g of the compound from example 1 and 0.048 g of an additional compound comprising three —O—(C=O)—

C≡C—H groups (Mn about 1000 g/mol) was added into a solution of DABCO (0.0058 g) in ethyl acetate (0.4 ml), and the mixture left exposed to the air at room temperature. After 2 hours, a brown, not sticky polymer was obtained (the cured inventive composition).

The additional compound was obtained by reacting a glycerine-propoxylated polyol with propiolic acid, wherein the OH:propiolic acid ratio is at least 1:1. The glycerine propoxylated polyol is produced by reacting glycerine with propylene oxide. Glycerine acts as the initiator.

Tensile tests (tensile speed 50 mm/min):
Elongation at break: 330%
Tensile strength: 3.38 MPa Example 4

Composition with compound from Example 1 (PITHF).

2 g of compound from example 1 was added into a solution of DABCO (0.005 g) in ethyl acetate (0.4 ml), and the mixture left exposed to the air at room temperature. After 2 hours, a pale brown, not sticky polymer was obtained.

Tensile tests (tensile speed 50 mm/min):
Elongation at break: 123%
Tensile strength: 1.66 MPa Example 5

Composition with compound from Example 2 (PHTHF).

2 g of compound from example 2 was added into a solution of DABCO (0.005 g) in ethyl acetate (0.4 ml), and the mixture left exposed to the air at room temperature. After 2 hours, a pale brown, not sticky polymer was obtained.

Tensile tests (tensile speed 50 mm/min):
Elongation at break: 60%
Tensile strength: 1.67 MPa Thermostability and Mechanical Properties Decomposition Temperatures (Td)

The following table shows the decomposition temperatures of cured compositions in accordance with some of the examples given above, and two further cured inventive compositions not described in detail but prepared in accordance with examples 4 and 5.

| Example | Decomposition temperature (° C.) |
|---|---|
| 5, PHTHF 2300 | 332.8 |
| 4, PHTHF 2300 | 318.3 |
| cured composition on the basis of a compound with IPDI as isocyanate and PTHF (Mn = 2000) as polyol | 317.7 |
| cured composition on the basis of a compound with methylene diphenyl diisocyanate (MDI) as isocyanate and PTHF (Mn = 1000) as polyol (hereafter PMTHF) | 304.1 |

As can be seen from the table above, the decomposition temperature of the cured inventive compositions is very high, in the shown cases higher than 300° C.

Elongation at Break/Tensile Strength

In the following tables, elongation at break/tensile strength for some inventive cured compositions is shown, wherein all compositions were prepared and cured as mentioned above.

Table 1 shows the influence of the isocyanate group on these properties (when maintaining the same polyol), Table 2 shows the influence of the molecular weight of the side chain (polyol), and Table 3 shows the influence of a further compound comprising three —O—(C=O)—C≡C—H groups (refer to example 1).

TABLE 1

Mechanical properties of cured compositions from different isocyanate conjugated PTHFs

| Cured composition on the basis of: * | DABCO Wt % | Elongation at break (%) | Tensile strength (MPa) |
|---|---|---|---|
| PMTHF (MDI, Mn~2300) | 0.1 | 26 | 1.24 |
| PHTHF (HDI, Mn~2300) | 0.3 | 59 | 1.67 |
| PITHF (IPDI, Mn~2300) | 0.3 | 123 | 1.66 |

All reactions were performed using 20 wt % of EtOAc based on the weight of the polymer. The content of the base (DABCO), and the solvent (EtOAc) are referred in wt. % are referred to the quantity of prepolymer.

TABLE 2

Mechanical properties of cured compositions from IPDI conjugated different molecular weight PTHFs

| Cured composition on the basis of: * | DABCO Wt % | Elongation at break (%) | Tensile strength (MPa) |
|---|---|---|---|
| PITHF, Mn~2300 | 0.3 | 123 | 1.66 |
| PITHF, Mn~4300* | 0.16 | 848 | 2.86 |

All reactions were performed using 20 wt % of EtOAc.
*In presence of PITHF 4300, 30 wt % of EtOAc were used. The content of the base (DABCO) and the solvent (EtOAc) are referred in wt. % are referred to the quantity of prepolymer.

TABLE 3

Mechanical properties of cured compositions from PITHF 2300 with different contents of a further compound comprising three —O—(C=O)—C≡C—H groups (see example 1).

| Polymer from: * | DABCO Wt % | Elongation at break (%) | Tensile strength (MPa) |
|---|---|---|---|
| PITHF MW~2300 | 0.3 | 123 | 1.66 |
| PITHF + further compound 5 mol % | 0.3 | 330 | 3.38 |
| PITHF + further compound 10 mol % | 0.3 | 94 | 1.81 |

All reactions were performed using 20 wt % of EtOAc.
The content of the base (DABCO), the solvent (EtOAc), and the further compound are referred in wt % are referred to the quantity of prepolymer.

As can be seen from the Tables 1 to 3 the inventive compounds/compositions/cured compositions offer a system with a very broad range of mechanical properties (elongation at break/tensile strength), i.e. with the inventive compounds/compositions/polymers a toolbox with a very broad field of applications is provided.

The invention claimed is:

1. A compound comprising at least two —(NH—C=O)— groups and at least two —(C=O)—C≡C—R$^1$ groups,
wherein the —(NH—C=O)— groups are provided by urea and/or urethane groups and R$^1$ represents hydrogen or a group having from 1 to 12 carbon atoms.

2. The compound according to claim 1, wherein the —(NH—C=O)— groups are provided by urethane groups.

3. The compound according to claim 1, obtained by
a) reacting a polyisocyanate with at least two isocyanate groups with a polyol or a polyamine or a mixture thereof to form an intermediate,
  wherein the molar ratio of the NCO groups of the polyisocyanate to the sum of hydroxyl groups, primary amino groups and secondary amino groups of the polyol and polyamine is less than 1; and
b) reacting a compound of the formula $R^2O$—(C=O)—C≡C—$R^1$ with the intermediate of step a) in molar excess to the sum of hydroxyl groups, primary amino groups and secondary amino groups of the intermediate,
wherein $R^1$ represents hydrogen or a group having from 1 to 12 carbon atoms, and $R^2$ represents hydrogen or a group having from 1 to 4 carbon atoms.

4. The compound according to claim 3, wherein the polyol is selected from a group comprising polyether polyols, polyether polyol block-copolymers, polyester polyols, polyester polyol block-copolymers or mixtures thereof and mixtures thereof.

5. The compound according to claim 3, wherein the polyol is selected from a group comprising polyethylene glycol, polypropylene glycol and polytetrahydrofuran, and mixtures thereof.

6. The compound according to claim 3, wherein the number average molar weight ($M_n$) of the polyol/polyamine from 1000 to 5000 g/mol.

7. The compound according to claim 3, wherein the polyisocyanate is selected from a group comprising 2,4-toluene diisocyanate, 2,6-toluene diisocyanate, 4,4'-diphenylmethane diisocyanate, 2,4'-diphenylmethane diisocyanate, 2,2'-diphenylmethane diisocyanate, isophorone diisocyanate, hexamethylene diisocyanate, 4,4'-methylene dicyclohexyl diisocyanate, 2,4'-methylene dicyclohexyl diisocyanate, 2,2'-methylene dicyclohexyl diisocyanate, and mixtures thereof.

8. A compound comprising at least two —(NH—C=O)— groups and at least two —(C=O)—C≡C—$R^1$ groups, wherein $R^1$ represents hydrogen or $CH_3$.

9. A curable composition comprising:
  a first unit comprising at least two —(NH—C=O)— groups,
  a second unit comprising at least two —(C=O)—C≡C—$R^1$ groups, and
  a catalyst,
  wherein $R^1$ represents hydrogen or a group having 1 to 12 carbon atoms.

10. The curable composition according to claim 9, wherein the —(NH—C=O)— groups are provided by urea and/or urethane groups.

11. The curable composition according to claim 9, wherein the first and the second units are part of one compound.

12. The curable composition according to claim 9, wherein the first and the second unit are part of different compounds.

13. The curable composition according to claim 9, wherein the first and the second unit are part of different compounds and the first unit is part of a thermoplastic polyurethane.

14. The curable composition according to claim 9, wherein the catalyst is a secondary or tertiary amine.

15. The curable composition according to claim 9, wherein the catalyst is selected from the group consisting of 1,4-diazabicyclo[2.2.2]octane, tetramethylethylenediamine, N,N-diisopropylethylamine, triethanolamine, tris(2-pyridylmethyl)amine, tributylamine, 4-dimethylaminophenol, N-ethyl-N-methyl propylamine, N-methyl piperidine, N-butyl-4-hydroxy piperidine, 1,8-diazabicyclo[5.4.0]undec-7-ene, 1,5-diazabicyclo[4.3.0]non-5-ene, imidazoline, benzimidazole, dimethylamino ethanol, pirrole, morpholine, piperidine, piperazine, indole, and mixtures thereof.

16. The curable composition according to claim 9, wherein the catalyst is 1,4-diazabicyclo[2.2.2]octane.

17. The curable composition according to claim 9, wherein the second unit is provided by a compound that is the reaction product of a polyether polyol with at least two OH groups with a compound of the formula $R^2O$—(C=O)—C≡C—$R^1$ in a quantity at least equivalent to two OH groups of the polyether polyol,
  wherein $R^1$ represents hydrogen or a group having 1 to 12 carbon atoms, and
  $R^2$ represents hydrogen or a group having 1 to 4 carbon atoms.

18. The curable composition according to claim 17, wherein the number average molar mass ($M_n$) of the compound comprising the second unit is from 500 to 1500 g/mol.

19. An adhesive, coating, casting composition or sealant comprising the composition of claim 9.

* * * * *